United States Patent [19]

Mitra et al.

[11] 4,386,068

[45] May 31, 1983

[54] ANTIHEMOPHILIC FACTOR CONCENTRATE AND METHOD FOR PREPARATION

[75] Inventors: Gautam Mitra, Kensington; John L. Lundblad, El Cerrito, both of Calif.

[73] Assignee: Cutter Laboratories, Inc., Berkeley, Calif.

[21] Appl. No.: 124,891

[22] Filed: Feb. 26, 1980

[51] Int. Cl.³ .............................................. A61K 35/14
[52] U.S. Cl. .................................................. 424/101
[58] Field of Search ........................................ 424/101

[56] References Cited

U.S. PATENT DOCUMENTS 4,170,639 10/1979 Liu ...................................... 424/101

OTHER PUBLICATIONS

Liu et al.—Vox Sang, vol. 38 (1980) pp. 216–221.

Primary Examiner—Sam Rosen
Attorney, Agent, or Firm—Theodore J. Leitereg

[57] ABSTRACT

Novel antihemophilic factor concentrates and process for making the same are disclosed. An aqueous solution of antihemophilic factor proteins is obtained, preferably by solubilizing antihemophilic factor proteins from blood plasma cryoprecipitate in water. The aqueous solution is purified to remove unwanted protein, for example, by mixing the aqueous solution with aluminum hydroxide. Then, the aqueous solution is ultrafiltered to concentrate it, mixed with buffer and saline and adjusted to an acid pH, and freeze-dried.

34 Claims, No Drawings

ANTIHEMOPHILIC FACTOR CONCENTRATE AND METHOD FOR PREPARATION

BACKGROUND OF THE INVENTION

1. Field of the Invention

This invention relates to and has among its objects the provision of novel antihemophilic factor concentrates and methods for making them. Further objects of the invention will be evident from the following description wherein parts and percentages are by weight unless specified otherwise.

2. Description of the Prior Art

Currently, antihemophilic factor (AHF), otherwise known as Factor VIII, is prepared from human plasma. Cryoprecipitate is recovered from thawed pools of fresh frozen human plasma by centrifugation and diced and washed to remove soluble proteins. Then, the cryoprecipitate is extracted or solubilized with water. The pH of the aqueous solution is adjusted to slightly acid and the solution is chilled to separate extraneous non-AHF protein. Next, the aqueous solution is treated with aluminum hydroxide to further remove unwanted protein, particularly prothrombin complex proteins. This purification technique using aluminum hydroxide has been described by Hershgold et al. in *J. Lab. & Clin. Med.*, 1966, Vol. 67, pages 23-32, by Mozen at the Twenty-Fourth Annual Wayne State University Symposium on Blood, Detroit, Mich. (January 1976) and at the XV Congress of the International Society of Hematology, Jerusalem, Israel (1974), and by Liu et al., U.S. Pat. No. 4,170,639 (October 1979). Salt and a buffer are added to the aqueous solution which is then freeze-dried after adjustment of the pH of the aqueous solution to slightly acid.

In large scale processing, it is desirable to remove water from the aqueous AHF solution prior to freeze-drying it. To this end the AHF concentrate is reprecipitated before it is lyophilized. The aqueous solution is treated with either cold ethanol, polyethylene glycol, or glycine which results in precipitation of AHF proteins. The precipitate is collected by centrifugation, mixed with water buffer, saline, and acid, and freeze-dried.

Liu, in U.S. Pat. No. 4,170,639, discloses that an aqueous AHF extract, after purification with aluminum hydroxide and reconstitution with buffer and saline and adjustment to an acidic pH, may be subjected to ultrafiltration to concentrate it prior to freeze-drying. The ultrafiltration is conducted only on reconstituted AHF extract that has been adjusted to an acidic pH using a membrane with a molecular weight cut-off of one million daltons.

SUMMARY OF THE INVENTION

We have discovered that water can be removed effectively from aqueous solutions of AHF proteins by subjecting an AHF solution to ultrafiltration after purifying it to remove unwanted proteins but prior to mixing it with buffer and saline and adjusting it to an acidic pH. Our studies have shown that water removal is achieved in the process of the invention without significant change in the activity of the AHF proteins. The ultrafiltration technique employed in the prior art processes causes a reduction in yield of AHF activity, which our method unexpectedly avoids.

A primary advantage of the present invention is that it results in essentially complete recovery of AHF activity. The conventional reprecipitation and ultrafiltration methods result in incomplete recoveries of Factor VIII activity, presumably due to denaturation of the AHF proteins. No significant reduction in AHF activity was observed in our process wherein ultrafiltration was applied to the aqueous extract prior to mixing with buffer and saline and pH adjustment for a period of at least five hours. The ultrafiltration process of the prior art results in about a 15% or more loss of antihemophilic factor.

Still another advantage of the present invention is the significantly higher content of Von Willebrandt factor (VIIIR:WF) in the product of our process. It is possible to obtain a product containing substantially the same proportions of VIIIR:WF and procoagulant factor (VIII:C). Such a product approaches more closely the native VIII:C state and should be suitable for Von Willebrandt patients, i.e., patients suffering from Von Willebrandt's disease. In addition, the in vivo half life of this product is increased. In general, the VIII:C/VIIIR:WF ratio in the products of the invention is within the range of about 1/0.5-1 and usually about 1/1, whereas in the alcohol precipitation method the above ratio is about 1/0.1-0.4, usually 1/0.2. The concentration of VIIIR:WF in the instant products is greater than 15 units per milliliter (ml), generally about 15-30 units per ml and sometimes as high as 100 units per ml. The concentrations of VIIIR:WF obtained with the alcohol precipitation step of concentration for example, generally are less than 15 units/ml, i.e., about 5-10 units/ml.

Another advantage of the invention is the improved ratio of AHF proteins to milligrams of fibrinogen. The increased yield of AHF concentrate over that obtained using conventional reprecipitation results in a significant decrease in the amount of fibrinogen per unit dose. Thus, fibrinogen overload in patients receiving large volumes of AHF concentrates may be avoided by using the products of our invention. The ratio of AHF proteins to milligrams of fibrinogen (VIII:C/mg. ∅) of the products of the invention falls within the range of about 2.6-4.0/1, usually about 3.0/1. In the alcohol reprecipitation method of concentration used by the art, the VIII:C/mg ∅ ratio of the final products is about 1.0-2.5/1, generally about 1.5/1. The present products having improved VIII:C/VIIIR:WF and VIII:C/mg ∅ heretofore have been unavailable.

DESCRIPTION OF THE PREFERRED EMBODIMENTS

As mentioned above, AHF concentrate is obtained from human plasma. In general, the preparation of AHF concentrate is carried out by modification and refinement of a method first described by Hershgold et al, *J. Lab. Clin. Med.*, supra. Cryoprecipitate is removed from pools of fresh frozen human plasma, which have been thawed at less than 5° C. The cryoprecipitate is diced and washed with buffer and then solubilized in water. The pH of the aqueous AHF solution is adjusted preferably to within the range of 6.40-6.95 by addition of a biologically acceptable acid, particular acids of this type being well known in the art. Any precipitate that forms after chilling the solution at less than 10° C. is removed by decantation or centrifugation. The aqueous solution containing the active AHF components is mixed with aluminum hydroxide to selectively remove unwanted proteins. It is a characteristic of this treatment that the pH remains virtually constant throughout.

As a result of the aluminum hydroxide treatment unwanted protein is selectively removed from the aqueous AHF solution without substantial loss of AHF potency. It is this purified aqueous solution to which the process of our invention is applied.

In accordance with the invention aqueous AHF solution processed as above is subjected to ultrafiltration. The solution is contacted with a particular semi-permeable membrane until the desired amount of water is removed, namely, that amount of water which, when removed, greatly facilitates the lyophilization of the final solution. Membranes suitable for the process of our invention should have a nominal molecular weight cut-off less than one million daltons, preferably within the range of 10,000 to 300,000 daltons. Membranes with molecular weight cut-offs of one million daltons physically entrap the AHF proteins and, thus, the yield of AHF concentrate is reduced. Typical ultrafiltration membranes that may be used in the invention (with corresponding nominal molecular weight cut-offs) are Amicon XM50 (50,000 daltons, manufactured by Amicon Corporation, Lexington, Mass.), Amicon PM10 (10,000 daltons), Amicon XM100A (100,000 daltons), Amicon XM300 (300,000 daltons), and the like. In a preferred embodiment of the invention ultrafiltration of the aqueous AHF solution is conducted with hollow fibers in an ultrafiltration unit such as for example, the Amicon DC 30 (30 sq. ft. filtration area) hollow fiber unit, using an ultrafiltration membrane such as the Amicon H10P10 (10,000 daltons) cartridge, or the equivalent.

It is preferred in carrying out the method of the invention that the laminar flow and shear rates at the ultrafiltration membrane wall be low. Excellent results are achieved with laminar flow rates at the wall less than Reynolds Number 2000, preferably within the range of Reynolds Number 200 to 300, and shear rates at the wall less than 1000 reverse seconds ($sec^{-1}$), preferably within the range of 200 to 300 $sec^{-1}$. It is to be realized, of course, that higher flow rates and the resulting shear at the membrane wall during ultrafiltration of the aqueous solution in accordance with the invention will yield a concentrated AHF product in a shorter processing time. However, the activity of the AHF concentrate is reduced at these higher rates due to AHF protein denaturation. In this respect, also, special care must be taken to minimize air uptake and other interfacial effects in a shear field such as foaming and the like in order to minimize denaturation of the AHF proteins.

The type of recirculation pump employed during the ultrafiltration procedure is an important aspect of the present invention. Diaphragm pumps (generally air-operated yield minimal denaturation of the AHF proteins whereas centrifugal pumps are undesirable because of excessive loss in AHF protein acitivity that results during their use. Suitable pumps to be used during the ultrafiltration step are, by way of example, Amicon LP-20 (Amicon Corporation) air pressure operated diaphragm pump and the Warren-Rupp Sandpiper pump (Model SA1-A-DB-1-SS) (Thomas and Associates, Corte Madera, Calif.).

Following ultrafiltration of the aqueous AHF solution the solution is mixed with buffer and saline as is conventional in the art. To this end aqueous sodium chloride is added to the aqueous extract in biologically-acceptable amounts usually to a level of 0.05–0.30 molar, preferably 0.15 molar. Furthermore, an appropriate biologically-acceptable buffer, such as sodium citrate, is added thereto to a level of 0.005–0.03 molar, preferably 0.01 molar. If necessary, the pH of the aqueous extract is adjusted to within the range 6.4 to 7.4 (established by regulation by the Food and Drug Administration) by addition of a biologically acceptable acid. The aqueous AHF solution is filtered to remove particles and then sterile filtered.

It is important to note that the ultrafiltration procedure for removing water from the aqueous AHF solution must be applied to the solution prior to mixing the solution with buffer and saline. If not, the benefits and advantages enumerated above are not realized, particularly with respect to yield of AHF product.

Following sterile filtration of the so-treated aqueous AHF solution, the solution is freeze-dried (lyophilized). The solution may be aseptically filled into containers of an appropriate size to be quick-frozen and the frozen material lyophilized under high vacuum as is well known in the art. The containers with freeze-dried product therein are sealed, and the product is stored at a temperature of about 2–8° C. until it is used.

For infusion, the contents of each container are reconstituted in sterile distilled water yielding a solution containing approximately 25 AHF activity units per milliliter.

It is within the purview of the invention to follow the above-described ultrafiltration procedure with a glycine precipitation step to improve the color and clarity of reconstituted final freeze-dried product. To this end the ultrafiltered aqueous solution is mixed with glycine to a concentration therein about 1.6–2.2 molar, preferably 1.9 molar, at a temperature of about 5–20° C. Optionally, the mixture can be mixed also with sodium citrate and saline to concentrations of 0.005–0.03 molar and 0.05–0.30 molar, respectively. The mixture is held for about 30 minutes or more, preferably 30–120 minutes, and optimally for 60 minutes. When the freeze-dried product, prepared in accordance with the above teaching, is reconstituted, it has a pale yellow color and a clarity greater than 80%.

It is noteworthy that the glycine precipitation step described above must be applied to ultrafiltered AHF solution. If the ultrafiltration step is omitted approximately one-half of the AHF activity is lost in the final product. Furthermore, in order that the glycine treatment be successful and that AHF activity loss be avoided, the aqueous AHF solution must contain at least 50 milligrams of protein per ml. prior to treatment with glycine.

The precipitate that forms as a result of the glycine treatment is separated from the AHF solution by conventional means such as centrifugation, filtration, and the like, and the precipitate is dissolved in buffer and saline as described hereinabove. After pH adjustment as above, the aqueous AHF solution is freeze-dried to yield a dried AHF concentrate.

It should be obvious that the ultrafiltered AHF solution with a reduced water content also may be considered to be an AHF concentrate, though not a completely dry one.

EXAMPLES

The invention is demonstrated further by the following illustrative examples.

In the examples total protein was determined by absorbance measurements as 280 nanometers.

Procoagulant activity (VIII:C) was assayed by one stage Activated Partial Thromboplastin Time (APTT)

test modified from the methods of Langdell et al., *J. Lab. Clin. Med.*, Vol. 41, pages 637–647 (1953) and Proctor et al., *Am. J. Clin. Path.*, Vol. 36, page 212 (1961).

Ristocetin-Willebrandt factor activity (VIIIR:WF) was assayed with gel-filtered platelets according to the method of Olson et al., *Am. J. Clin. Path.*, Vol. 63, pages 210–218 (1975).

Quantitative factor VIII antigen (VIIIR:Ag) determinations were done according to the procedure of Laurell, *Anal. Biochem.*, Vol. 15, pages 45–52 (1966).

Antiserum against the Factor VIII related proteins was obtained from Behring Diagnostics (Sommerville, N.J.).

Protein species distribution was assayed by cellulose acetate electrophoresis.

EXAMPLE 1

Production of Aqueous Solution of AHF Proteins

A modified method of Hershgold et al., supra, was followed. Fresh frozen human plasma was thawed at not more than 5° C. and warmed to not more than 15° C. The so-warmed plasma was chilled to 2° C. After 3 hours the insoluble cryoprecipitate was collected by centrifugation at not more than 10° C.

The cryoprecipitate (1 kg.) was diced and suspended in 10 l. of sterile water at 32° C. for not more than 2 hours. Then, the mixture was adjusted to pH 6.8 by addition of 0.1 N hydrochloric acid and chilled to 5° C. Precipitate was removed by centrifugation at 5° C.

The aqueous solution (supernatant) was mixed with a 3% suspension of aluminum hydroxide in water in the ratio of 0.1 g of aluminum hydroxide per 1 g of protein. The mixture was stirred for 30 min. at 5° C. and the aluminum hydroxide was removed by filtration and centrifugation.

EXAMPLE 2

Ultrafiltration of AHF Solution in Thin Channels

The aqueous solution (300 ml.) from Example 1 was ultrafiltered through a variety of thin channel ultrafiltration membranes in an Amicon TCF-10 thin-channel system at the specified temperature until concentrated to a volume of 50 ml. The membranes employed were the Amicon XM50, Amicon XM100A, and Amicon XM300 (all Amicon Corporation), Millipore PSVP ($10^6$ daltons, Millipore Corporation, Bedford, Mass.). The ultrafiltered material was analyzed by the above-described method.

The results are summarized in Table 1.

EXAMPLE 3

Ultrafiltration if AHF Solution in Hollow Fibers Pilot Scale Runs

Aqueous AHF solution (20 l) prepared as described in Example 1 was ultrafiltered in an Amicon DC30 hollow fiber unit using Amicon H10P10 cartridges with an effective filtration area of 10 sq. ft. per cartridge and a minimal molecular retention limit of 10,000 daltons until the solution was concentrated to a volume of 4 l.

The results in Table 2 were observed upon analysis of the ultrafiltered material pursuant to the above-described methods.

TABLE 1

| Run No. | Membrane Used | T (°C.) | Feed Solution $A_{280}{}^a$ | Feed Solution Sp. Act.[b] (VIII:C/$A_{280}$) | Concentrate $A_{280}{}^a$ | Concentrate Sp. Act.[b] (VIII:C/$A_{280}$) | Filtrate $A_{280}{}^a$ |
|---|---|---|---|---|---|---|---|
| 1 | XM50 | 25 | 5.17 | 1.24 | 27.19 | 1.09 | 0.50 |
| 2 | XM50 | 25 | 5.01 | 0.56 | 19.23 | 0.61 | 0.52 |
| 3 | XM100A | 25 | 3.71 | 1.11 | 16.91 | 1.22 | 0.22 |
| 4 | XM100A | 5 | 5.76 | 0.76 | 9.31 | 0.73 | 0.38 |
| 5 | XM300 | 25 | 5.37 | 0.73 | 23.96 | 0.77 | 0.30 |
| 6 | PSVP | 25 | 5.48 | 0.78 | 33.17 | $0.82^c$ | 0.63 |

[a]Absorbance at 280 nanometers.
[b]Specific activity indicated by units of biological activity per total protein content.
[c]Although the specific activity in clear solution remained the same, 15% of total VIII:C activity was lost in the precipitate which formed.

TABLE 2

| Run No. | Feed Solution VIII-C (U/ml)[a] | Feed Solution VIII:WF (U/ml)[a] | Feed Solution VIIIR:Ag (U/ml)[a] | Feed Solution $A_{280}$ | Feed Solution Sp. Act. (VIIIC/$A_{280}$) | Concentrate VIII-C (U/ml)[a] | Concentrate VIIIR:-WF (U/ml)[a] | Concentrate VIIIR:Ag (U/ml)[a] | Concentrate $A_{280}$ | Concentrate Sp. Activity (VIIIC/$A_{280}$) |
|---|---|---|---|---|---|---|---|---|---|---|
| 1 | 3.74 | 4.73 | 8.15 | 5.63 | 0.66 | 26.00 | 29.10 | 56.25 | 33.20 | 0.78 |
| 2 | 4.34 | 3.50 | 8.0 | 5.86 | 0.74 | 27.14 | 19.23 | 46.01 | 29.93 | 0.91 |
| 3 | 4.00 | 3.33 | 6.88 | 5.97 | 0.67 | 23.24 | 14.90 | 26.30 | 24.87 | 0.93 |
| 4 | 3.40 | 2.96 | 5.79 | 6.01 | 0.57 | 31.82 | 33.99 | 73.49 | 47.98 | 0.66 |
| 5 | 2.90 | 3.20 | 6.30 | 6.48 | 0.45 | 23.95 | 47.34 | 58.92 | 44.39 | 0.66 |
| 6 | 4.04 | 1.80 | N/A[b] | 5.75 | 0.70 | 37.79 | 32.59 | N/A[b] | 46.76 | 0.81 |
| 7 | 3.40 | 2.96 | N/A[b] | 6.20 | 0.55 | 37.46 | 37.32 | N/A[b] | 48.77 | 0.77 |
| 8 | 4.0 | N/A[b] | N/A[b] | 5.20 | 0.77 | 44.22 | N/A[b] | N/A[b] | 46.89 | 0.94 |
| 9 | 3.7 | N/A[b] | N/A[b] | 5.08 | 0.73 | 42.16 | N/A[b] | N/A[b] | 45.97 | 0.92 |
| 10 | 4.9 | N/A[b] | N/A[b] | 5.00 | 0.98 | 44.80 | N/A[b] | N/A[b] | 44.30 | 1.01 |

[a]U/ml = Units of activity per milliliter.
[b]N/A = not assayed

The ultrafiltered material was mixed with sodium citrate and sodium chloride in an amount sufficient to attain a level of 0.15 molar sodium chloride and 0.01 molar sodium citrate. Next, the pH of the constituted material was adjusted to 6.9 by addition of 1 N hydrochloric acid. Then, 10 ml. each of constituted material was placed in vials and freeze-dried at a pressure lower than 400 microns and a starting shelf temperature of −40° C. to completion shelf temperature of +30° C.

EXAMPLE 4

Ultrafiltration of AHF Solution in Hollow Fibers—Production Scale Runs

Aqueous AHF solution prepared as described in Example 1 was ultrafiltered in an Amicon DC hollow fiber unit using Amicon H10P10 cartridge.

The results of three runs are tabularized below.

TABLE 3

| | Production Scale Ultrafiltration Runs | | | | VIII-C |
|---|---|---|---|---|---|
| | Feed Solution | | Concentrate | | |
| Run No. | Volume (l) | VIII-C (U/ml)[a] | Volume (l) | VIII-C (U/ml)[a] | Recovery (%) |
| 1 | 99.95 | 4.45 | 9.80 | 39.00 | 86 |
| 2 | 92.60 | 3.40 | 8.93 | 37.50 | 106 |
| 3 | 92.16 | 5.80 | 16.67 | 27.80 | 87 |

[a]U/ml = Units of activity per milliliter.

EXAMPLE 5

Protein Species Distribution in Ultrafiltered Concentrate

The ultrafiltered concentrates from Example 3, Runs 1, 2 and 3, respectively, were subjected to cellulose acetate electrophoresis to determine protein species distribution.

The results are summarized in the following Table 4.

TABLE 4

| | Protein Species Distribution in Ultrafiltered Concentrate | | | | | | | | | | | | |
|---|---|---|---|---|---|---|---|---|---|---|---|---|---|
| | Feed Solution | | | | | | Concentrate | | | | | | |
| Run No. | Albumin | Globulin | | | | | VIII:C per mg. fibrinogen | Albumin | Globulin | | | | | VIII:C per mg. fibrinogen |
| | | $\alpha_1$ | $\alpha_2$ | $\beta_1$ | $\gamma$ | $\emptyset^a$ | | | $\alpha_1$ | $\alpha_2$ | $\beta_1$ | $\gamma$ | $\emptyset^a$ | |
| 1 | 47.5 | 0.3 | 18.0 | 4.5 | 1.9 | 27.8 | — | 39.5 | 1.0 | 23.5 | 4.2 | 2.2 | 29.6 | 3.44 |
| 2 | 38.1 | — | 23.7 | 2.3 | — | 35.8 | — | 33.9 | 1.0 | 25.2 | 3.9 | 1.8 | 34.3 | 3.44 |
| 3 | 36.1 | 0.3 | 27.7 | 4.0 | — | 31.9 | — | 34.6 | 0.6 | 27.1 | 4.1 | — | 33.6 | 3.62 |

[a]Fibrinogen and $\beta_2$ globulin have similar mobilities; the sum of which is shown as $\emptyset$.

EXAMPLE 6

Ultrafiltration of AHF Solution Followed by Glycine Precipitation

Ultrafiltered AHF solution (8.6 l) prepared as described in Example 4 was cooled to 12° C. and mixed with sodium citrate to a concentration of 0.01 molar, with sodium chloride to a concentration of 0.15 molar, and with glycine to a concentration of 1.9 molar. The temperature of the mixture was lowered to 5° C. and maintained at 5° C. throughout the treatment. After 1 hr. the mixture was centrifuged at 5° C. in a Static mode at 8500xg for 30 minutes, and a paste was separated from effluent.

The paste from glycine treatment was dissolved in final container buffer system (0.01 M sodium citrate and 0.15 M saline), and a portion of the solution was analyzed according to the aforementioned procedures.

The remaining portion of the above solution was frozen at −70° C. for 30 days, thawed, and analyzed as above.

The results are summarized in the table below.

| Sample | $A_{280}$ | VIII:C ($\mu$/ml) | VIIIR:WF ($\mu$/ml) |
|---|---|---|---|
| Ultrafiltered solution | 80.60 | 45.8 | 44.25 |
| Dissolved paste after glycine treatment | 47.10 | 33.6 | 39.0 |
| after freezing & thawing | 47.10 | 31.7 | 35.0 |

The frozen solution from above was thawed and prefiltered. Dextrose was added to a level of 1%, and the pH of the solution was adjusted to 6.9 by addition of 1 M hydrochloride acid. The solution was filtered through 0.45$\mu$/0.22$\mu$ Pall filters to a sterile bulk tank, from which 10 ml. each of the solution was placed in vials. The contents of the vials were freeze-dried in a Stokes freeze-dryer as described above.

Freeze-dried product from one vial was constituted in final container buffer and analzyed as described above. The following results were obtained:
Specific activity (VIII:C basis): 0.89.
Solubility time: 30 min., 38 sec.
VIIIR:WF ($\mu$/ml) (1:100 dilution): 22.5.
VIIIR:Ag ($\mu$/ml)(1:200 dilution): 81.
Clarity: >80%.

Clarity was measured by determining transmittance of the sample at 580 nanometers. The control or standard was water, and clarity was expressed as transmittance of sample (580)/transmittance of water (580)×100.

Having thus described the invention, what is claimed is:

1. A process for the production of antihemophilic factor concentrate, comprising the steps of
   (a) subjecting an aqueous solution of antihemophilic factor proteins to purification,
   (b) subjecting the purified aqueous solution of antihemophilic factor of step (a) to ultrafiltration to remove water, and
   (c) mixing the concentrated aqueous solution of antihemophilic factor of step (b) with buffer and saline.

2. The process of claim 1 which further includes the step of freeze-drying the ultrafiltered aqueous solution of step (c).

3. The process of claim 1 wherein the aqueous solution of antihemophilic factor proteins is purified in step (a) by mixing with an aluminum hydroxide adsorbent.

4. The process of claim 3 wherein the pH of the mixture is acidic.

5. The process of claim 1 wherein the ultrafiltration is conducted using an ultrafiltration membrane having a nominal molecular weight cut-off less than one million daltons.

6. The process of claim 1 wherein the ultrafiltration is conducted using an ultrafiltration membrane having a nominal molecular weight cut-off within the range of 10,000 to 300,000 daltons.

7. The process of claim 1 wherein the ultrafiltration is conducted using a hollow fiber ultrafiltration membrane.

8. The process of claim 1 wherein the ultrafiltration is conducted with a laminar flow rate at the ultrafiltration membrane wall less than Reynolds Number 2000.

9. The process of claim 1 wherein the ultrafiltration is conducted with a shear rate at the ultrafiltration membrane wall less than 2000 reverse seconds.

10. The process of claim 1 wherein the ultrafiltration is conducted using a diaphragm pump.

11. The process of claim 1 which further includes the step of mixing the ultrafiltered aqueous solution with glycine to further purify it.

12. The process of claim 11 wherein the ultrafiltered aqueous solution is mixed with glycine prior to mixing it with buffer and saline.

13. The process of claim 1 wherein the aqueous solution of antihemophilic factor proteins is obtained by solubilizing antihemophilic factor proteins from blood plasma cryoprecipitate in aqueous medium.

14. The process of claim 1 which further includes the step of adjusting the aqueous solution of step (c) to a slightly acid pH by addition of acid.

15. A process for the production of antihemophilic factor concentrate, comprising the steps of
(a) subjecting an aqueous solution of antihemophilic blood plasma cryoprecipitate to purification using an aluminum hydroxide adsorbent,
(b) subjecting the purified aqueous solution of antihemophilic factor of step (a) to ultrafiltration to remove water,
(c) mixing the concentrated solution of antihemophilic factor of step (b) with buffer and saline and adjusting to an acid pH, and then
(d) freeze-drying the mixture.

16. The process of claim 15 wherein the ultrafiltration is conducted using an ultrafiltration membrane having a nominal molecular weight cut-off less than one million daltons.

17. The process of claim 15 wherein the ultrafiltration is conducted using an ultrafiltration membrane having a nominal molecular weight cut-off within the range of 10,000 to 300,000 daltons.

18. The process of claim 15 wherein the ultrafiltration is conducted using a hollow fiber ultrafiltration membrane.

19. The process of claim 15 wherein the ultrafiltration is conducted with a laminar flow rate at the ultrafiltration membrane wall less than Reynolds Number 2000.

20. The process of claim 15 wherein the ultrafiltration is conducted with a shear rate at the ultrafiltration membrane wall less than 2000 reverse seconds.

21. The process of claim 15 wherein the ultrafiltration is conducted using a diaphragm pump.

22. The process of claim 15 which further includes the step of mixing the ultrafiltered aqueous solution with glycine to further purify it.

23. The process of claim 22 wherein the ultrafiltered aqueous solution is mixed with glycine prior to mixing it with buffer and saline.

24. In the process for the production of antihemophilic factor concentrate in purified form wherein an aqueous solution of antihemophilic blood plasma cryoprecipitate is subjected to purification by mixing with an aluminum hydroxide adsorbent and by precipitating unwanted protein in the cold and wherein the aqueous solution containing antihemophilic factor is mixed with buffer and saline and adjusted to an acid pH, and wherein the aqueous solution containing antihemophilic factor is freeze-dried, the improvement which comprises concentrating the aqueous solution containing antihemophilic factor by removal of water prior to mixing it with buffer and saline.

25. Process according to claim 24, where the water is removed by subjecting the aqueous extract to ultrafiltration.

26. Process according to claim 25, where the water is removed by means of a semi-permeable membrane.

27. The process of claim 24 wherein the ultrafiltration is conducted using an ultrafiltration membrane having a nominal molecular weight cut-off less than one million daltons.

28. The process of claim 24 wherein the ultrafiltration is conducted using an ultrafiltration membrane having a nominal molecular weight cut-off within the range of 10,000 to 300,000 daltons.

29. The process of claim 24 wherein the ultrafiltration is conducted using a hollow fiber ultrafiltration membrane.

30. The process of claim 24 wherein the ultrafiltration is conducted with a laminar flow rate at the ultrafiltration membrane wall less than Reynolds Number 2000.

31. The process of claim 24 wherein the ultrafiltration is conducted with a shear rate at the ultrafiltration membrane wall less than 2000 reverse seconds.

32. The process of claim 24 wherein the ultrafiltration is conducted using a diaphragm pump.

33. The process of claim 24 which further includes the step of mixing the ultrafiltered aqueous solution with glycine.

34. The process of claim 33 wherein the ultrafiltered aqueous solution is mixed with glycine prior to mixing it with buffer and saline.

* * * * *

UNITED STATES PATENT AND TRADEMARK OFFICE
CERTIFICATE OF CORRECTION

PATENT NO. : 4,386,068
DATED : May 31, 1983
INVENTOR(S) : Gautam Mitra and John L. Lundblad It is certified that error appears in the above-identified patent and that said Letters Patent are hereby corrected as shown below:

Title Page, Section [75], change

"Inventors: Gautam Mitra, Kensington;
John L. Lundblad, El Cerrito,
both of Calif."

to

--Inventors: Gautam Mitra, Kensington;
John L. Lundblad, El Cerrito;
and Duane D. Schroeder, Orinda,
all of Calif.--

Signed and Sealed this

Seventeenth Day of July 1984

[SEAL]

Attest:

GERALD J. MOSSINGHOFF

Attesting Officer    Commissioner of Patents and Trademarks